United States Patent
Baarman et al.

(10) Patent No.: US 7,116,200 B2
(45) Date of Patent: Oct. 3, 2006

(54) INDUCTIVE COIL ASSEMBLY

(75) Inventors: David W. Baarman, Fennville, MI (US); Terry L. Lautzenheiser, Nunica, MI (US)

(73) Assignee: Access Business Group International LLC, Ada, MI (US)

( * ) Notice: Subject to any disclaimer, the term of this patent is extended or adjusted under 35 U.S.C. 154(b) by 0 days.

(21) Appl. No.: 11/115,855

(22) Filed: Apr. 27, 2005

(65) Prior Publication Data

US 2005/0189882 A1    Sep. 1, 2005

Related U.S. Application Data

(60) Division of application No. 10/689,224, filed on Oct. 20, 2003, which is a continuation-in-part of application No. 10/357,932, filed on Feb. 4, 2003.

(51) Int. Cl.
*H01F 27/02* (2006.01)
(52) U.S. Cl. .................... 336/98; 336/192; 336/210
(58) Field of Classification Search ................ 336/98, 336/183, 184
See application file for complete search history.

(56) References Cited

U.S. PATENT DOCUMENTS

| | | | |
|---|---|---|---|
| 4,287,809 A | | 9/1981 | Egli et al. |
| 4,779,068 A | * | 10/1988 | Sakamoto et al. .......... 333/176 |
| 4,939,494 A | * | 7/1990 | Masuda et al. ............. 336/96 |
| 5,047,715 A | | 9/1991 | Morgenstern |
| 5,281,941 A | | 1/1994 | Bernstein |
| 5,781,287 A | | 7/1998 | Heinzl et al. |
| 5,814,900 A | | 9/1998 | Esser et al. |
| 5,913,820 A | | 6/1999 | Bladen et al. |
| 6,597,076 B1 | | 7/2003 | Scheible et al. |
| 2002/0118004 A1 | | 8/2002 | Scheible et al. |
| 2003/0062980 A1 | | 4/2003 | Garrels et al. |

FOREIGN PATENT DOCUMENTS

| | | |
|---|---|---|
| DE | 2732950 | 2/1979 |
| DE | 3412237 | 10/1985 |
| EP | 1174082 | 1/2002 |
| GB | 2326769 | 12/1998 |
| JP | 2001 327109 | 11/2001 |
| WO | WO 01/67046 | 9/2001 |

* cited by examiner

*Primary Examiner*—David Vu
(74) *Attorney, Agent, or Firm*—Warner Norcross & Judd

(57) ABSTRACT

An inductive coil assembly having multiple coils arranged at distinct orientations to provide efficient inductive coupling of power or communications or both to a device when the device is arranged at different orientations with respect to the inductive primary coil. In one embodiment, the inductive coil assembly includes three coils, each oriented along one of the x, y and z axes of a standard Cartesian three-dimensional coordinate system. The three separate coils provide effective transfer of power and communication when the device is at essentially any orientation with respect to the primary coil. In an alternative embodiment, the multi-axis inductive coil assembly of the present invention can function as a primary to inductively transmit power or communication or both over a plurality of magnetic fields at distinct orientations.

8 Claims, 16 Drawing Sheets

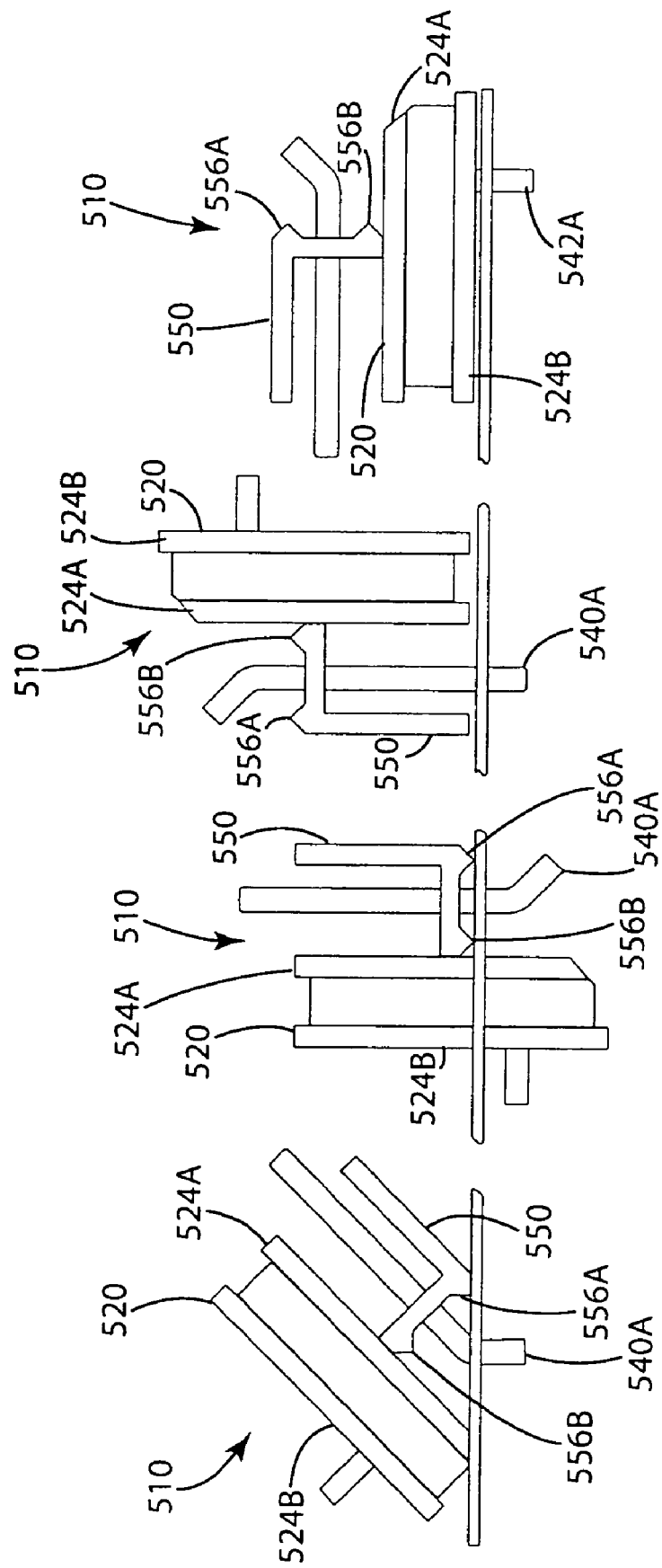

INDUCTIVE COIL ASSEMBLY

The present invention is a division of application U.S. application Ser. No. 10/689,224, filed Oct. 20, 2003, which is a continuation-in-part of U.S. patent application Ser. No. 10/357,932, entitled "Inductively Powered Apparatus," which was filed on Feb. 4, 2003.

BACKGROUND OF THE INVENTION

The present invention relates to the inductive transfer of power and communications, and more particularly to methods and apparatus for receiving inductively transmitted power and communications.

The principles of inductive power transfer have been known for many years. As a result of mutual inductance, power is wirelessly transferred from a primary coil (or simply "primary") in a power supply circuit to a secondary coil (or simply "secondary") in a secondary circuit. The secondary circuit is electrically coupled with a device, such as a lamp, a motor, a battery charger or any other device powered by electricity. The wireless connection provides a number of advantages over conventional hardwired connections. A wireless connection can reduce the chance of shock and can provide a relatively high level of electrical isolation between the power supply circuit and the secondary circuit. Inductive couplings can also make it easier for a consumer to replace limited-life components. For example, in the context of lighting devices, an inductively powered lamp assembly can be easily replaced without the need to make direct electrical connections. This not only makes the process easier to perform, but also limits the risk of exposure to electric shock.

The use of inductive power transfer has, however, for the most part been limited to niche applications, such as for connections in wet environments. The limited use of inductive power transfer has been largely the result of power transfer efficiency concerns. To improve the efficiency of the inductive coupling, it is conventional to carefully design the configuration and layout of the primary and secondary coils. The primary and the secondary are conventionally disposed within closely mating components with minimal gap between the primary and the secondary. For example, the primary is often disposed within a base defining a central opening and the secondary is often disposed within a cylindrical component that fits closely within the central opening of the base. This and other conventional constructions are design to provide close coaxial and radial alignment between the primary coil and the secondary coil. Several specific examples of patents that reflect the conventional approach of providing a fixed, predetermined physical relationship between the primary and secondary coils include: U.S. Pat. No. 5,264,997 to Hutchisson et al, which discloses an inductive lamp with coaxial and closely interfitting primary and secondary coils; U.S. Pat. No. 5,536,979 to McEachern et al, which discloses an inductive charging device in which the device to be charged is fitted closely within a cradle to position the coils in a fixed, predetermined relationship; U.S. Pat. No. 5,949,155 to Tamura et al, which discloses a shaver with adjacent inductive coils set in a fixed relationship; U.S. Pat. No. 5,952,814 to Van Lerberghe, which discloses an inductive charger for a telephone wherein the physical relationship between the primary and secondary coils is fixed; and U.S. Pat. No. 6,028,413 to Brockman, which discloses a charging device having a mechanical guide for ensuring precise, predetermined alignment between the inductive coils. The conventional practice of providing precise alignment between the primary and secondary coil has placed significant limitation on the overall design and adaptability of inductively powered devices.

SUMMARY OF THE INVENTION

The aforementioned problems are overcome by the present invention wherein a device is provided with an inductive coil assembly having a plurality of secondary coils that are each arranged in a different orientation. The multiple coils permit the device to efficiently receive power or communications or both when the device is disposed at different orientations with respect to the primary.

In one embodiment, the inductive coil assembly includes three coils that are arranged along the x, y and z axes of a standard Cartesian coordinate system. In this embodiment, efficient power and communications transfer is obtainable regardless of the orientation of the device within the primary.

In another embodiment, the inductive coil assembly includes a single set of coils to receive power and to send and receive communications. In this embodiment, the power signal functions as a carrier signal for the communications. In an alternative embodiment, separate coils can be provided for power and communication. For example, a first set of z, y and z coils can be provided to receive power and a second set of x, y and z coils can be provided to receive communications.

In one embodiment, the inductive coil assembly includes a one-piece bobbin that facilitates manufacture and assembly of the inductive coil assembly. The bobbin includes a separate spool with winding guides along each of the three axes and is designed to permit molding without the need for slides, pins or other complex mold tools.

In another embodiment, the inductive coil assembly can be used as a primary to transmit power or communication or both to a second. The inductive coil assembly with different coils at different orientations can generate magnetic fields at different orientation and thereby provide sufficient inductive coupling when an inductive device with only a single secondary coil is at different orientations.

In applications where only a single coil is used, it is possible that a device randomly placed within a magnetic field will be located with the coil oriented substantially parallel to the magnetic field. In such situations, the secondary may not receive sufficient power to power the device from the primary. The use of multiple coils addresses this problem by providing a secondary coil arrangement that significantly increases the likelihood that at least one coil will at least substantially intersect the flux lines of the magnetic field generated by the primary. For example, an inductive device may include a secondary with two coils that are oriented at 90 degrees to one another. With this configuration, at least one of the two coils is likely to extend across the flux lines of the magnetic field and receive power from the primary. The number of separate coils may vary from application to application, for example, the inductive device may include 3, 4, 6 or 8 coils at different orientations to provide improved efficiency in a wide variety of orientations. By providing a sufficient number of coils at different orientations, the inductive device can be configured to receive power from the primary regardless of the orientation of the inductive device.

The present invention provides a simple and inexpensive inductive coil assembly that improves the efficiency of inductive systems when precise primary/secondary alignment does not exist. The present invention permits power and communications to be transferred inductively in an environment where the position of the secondary within the primary may vary. The inductive coil assembly is manufactured on a bobbin that provides winding guides along all three axes, yet is easily manufactured without complex slide, pins or other complex mold tools.

These and other objects, advantages, and features of the invention will be readily understood and appreciated by reference to the detailed description of the preferred embodiment and the drawings.

BRIEF DESCRIPTION OF THE DRAWINGS

FIGS. 12a–d are perspective views of a fourth alternative bobbin showing the bobbin is different mounting position.

DETAILED DESCRIPTION OF THE PREFERRED EMBODIMENT

An inductive coil assembly 10 manufactured in accordance with an embodiment of the present invention is shown in FIGS. 1a–d. The inductive coil assembly 10 generally includes three separate coils 12, 14 and 16 that are arranged at separate orientations with respect to one another. The separate coils 12, 14 and 16 may be electrically connected to a device through an inductive control circuit. The separate coils 12, 14 and 16 may be wrapped around a one-piece bobbin 20 that facilitates the manufacture and assembly of the present invention. Although the present invention is described in connection with a three-coil embodiment, the number of coils may vary.

As noted above, the inductive coil assembly 10 includes a bobbin 20 for supporting the various coils 12, 14 and 16. In one embodiment, the bobbin 20 is a one-piece structure that is specially designed for easy manufacture and easy assembly of the inductive coil assembly 10. In the illustrated embodiment, the bobbin 20 is configured to support three separate coils 12, 14 and 16 arranged substantially orthogonally with respect to one another. More specifically, the bobbin 20 accommodates three coils 12, 14 and 16, one oriented about each of the x, y and z axes of a Cartesian three-dimensional coordinate system. In the illustrated embodiment, the bobbin 20 also includes a pair of electrical pins 62a–b, 64a–b and 66a–b for electrically connecting opposite ends of each coil to a circuit board (not shown).

Figure 1A:
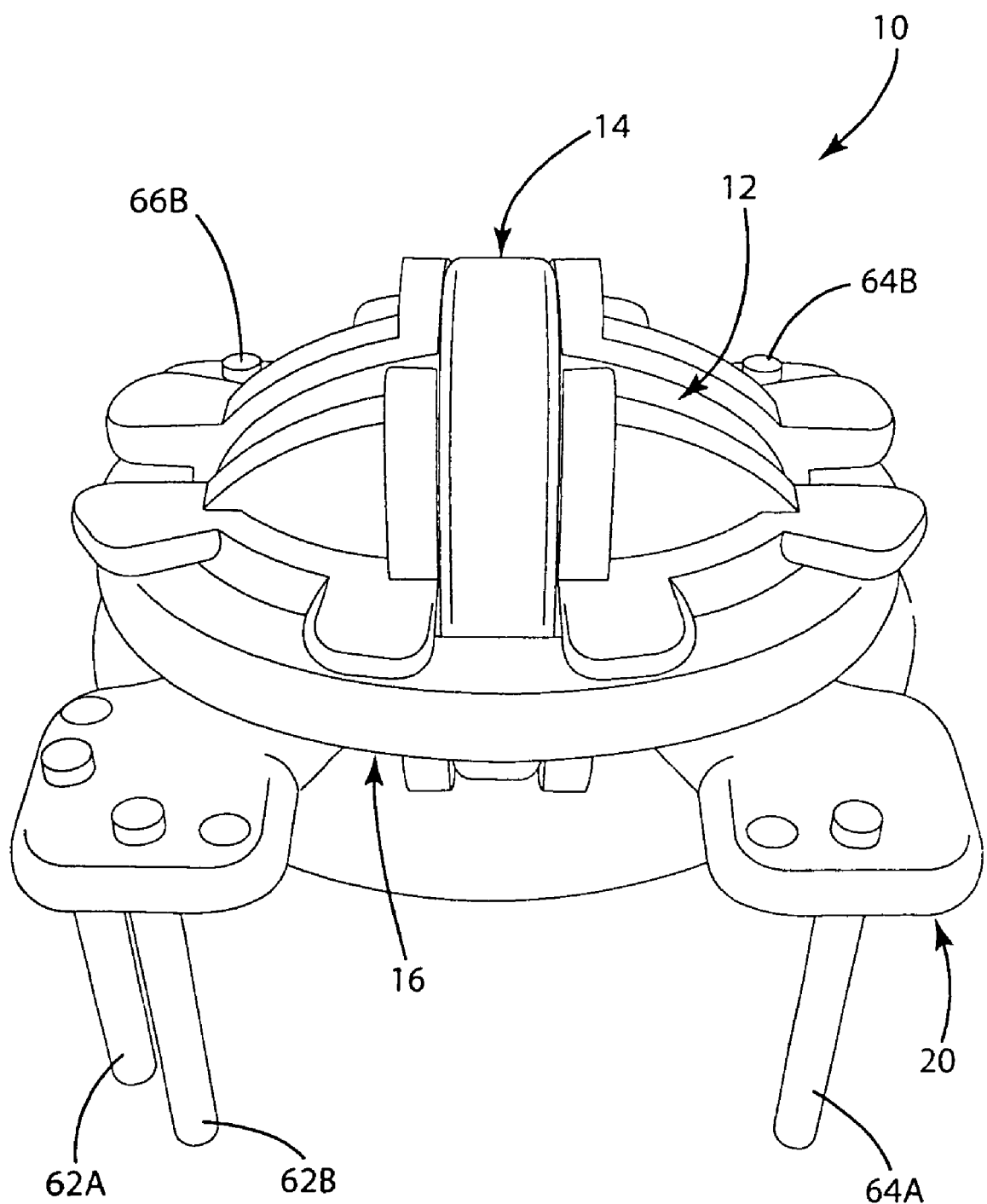
FIG. 1a is a perspective view of an inductive coil assembly in accordance with an embodiment of the present invention.
Figure 1B:
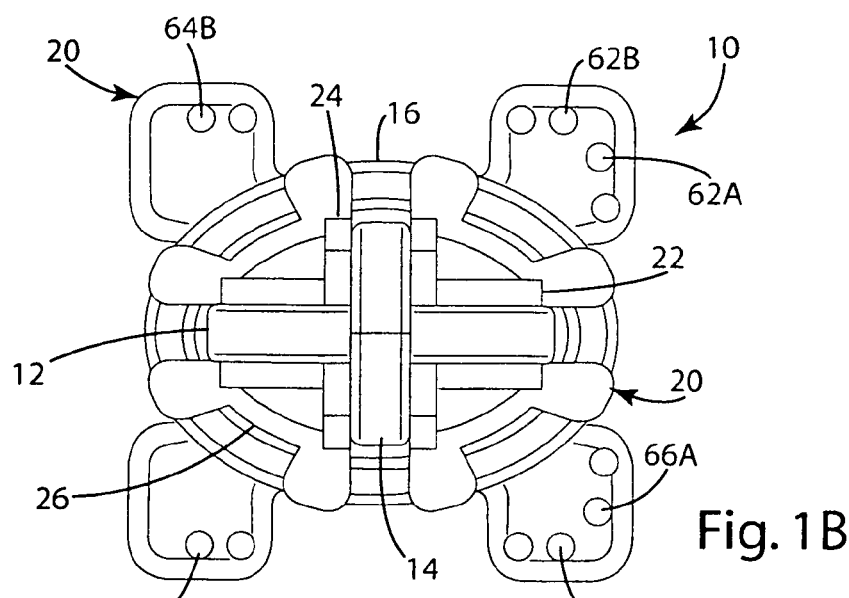
FIG. 1b is a top plan view of the inductive coil assembly.
Figure 1C:
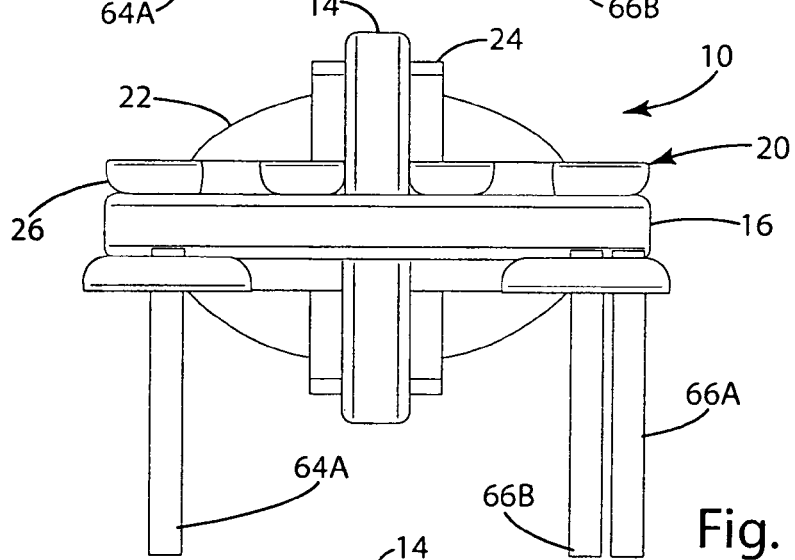
FIG. 1c is a front plan view of the inductive coil assembly.
Figure 1D:
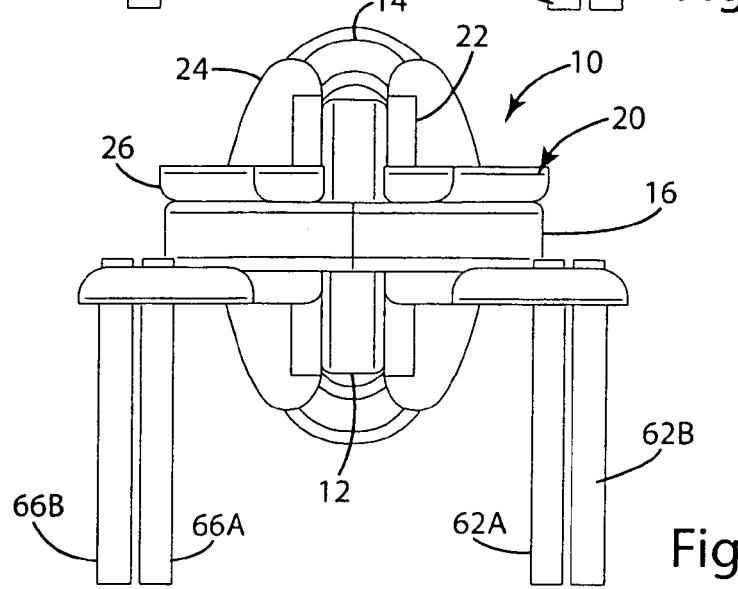
FIG. 1d is a side elevational view of the inductive coil assembly.
Figure 2:
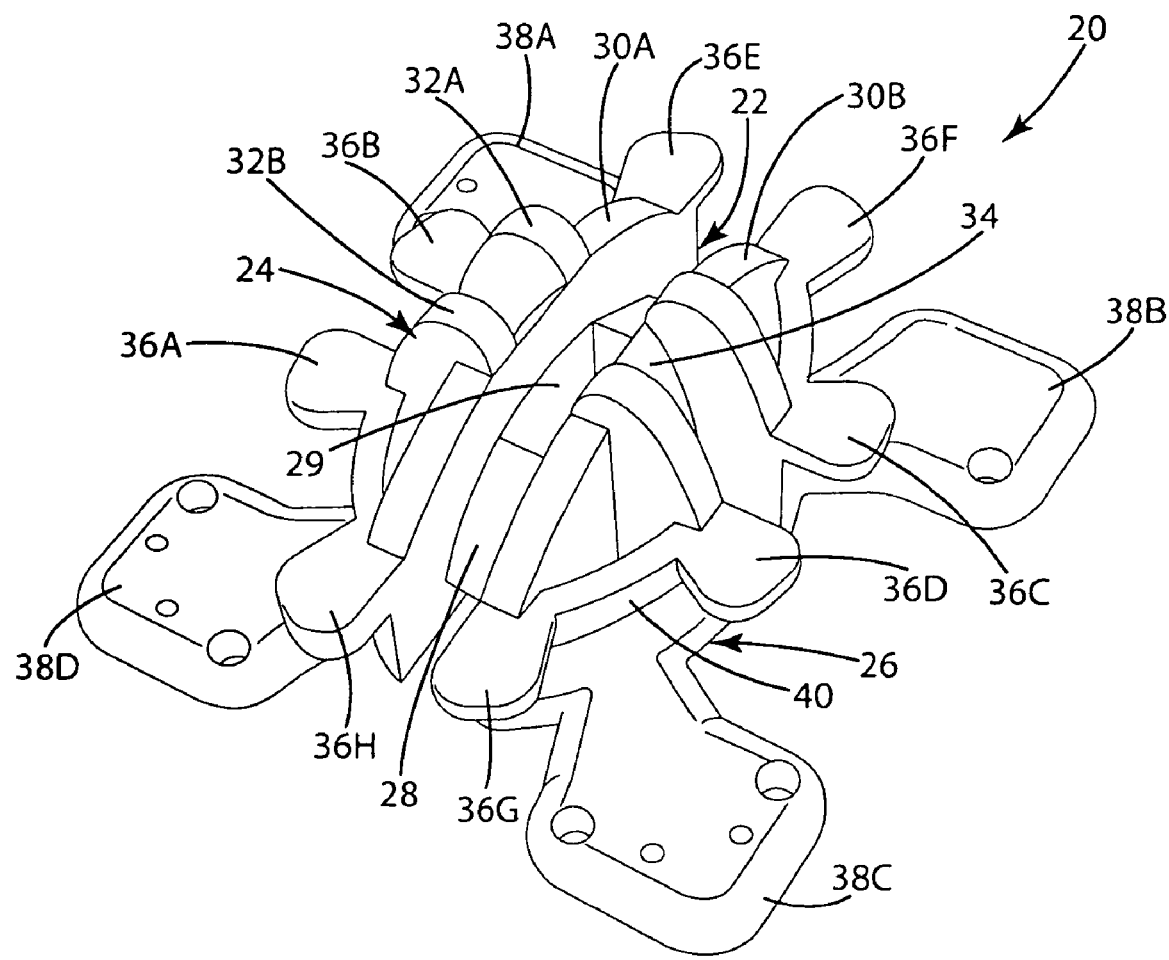
FIG. 2 is a perspective view of a bobbin in accordance with an embodiment of the present invention.
Figure 3:
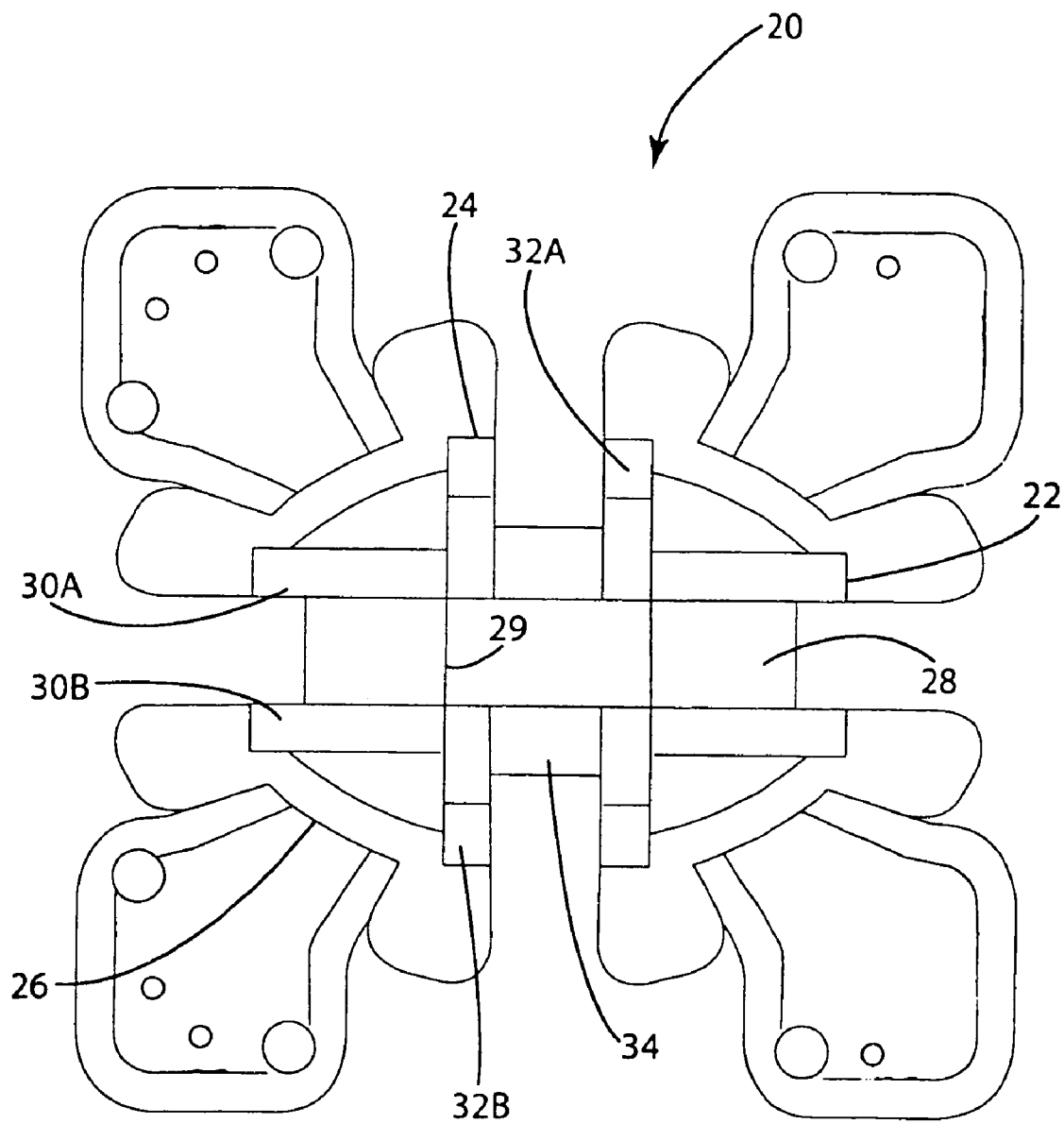
FIG. 3 is a top plan view of the bobbin.
Figure 4:
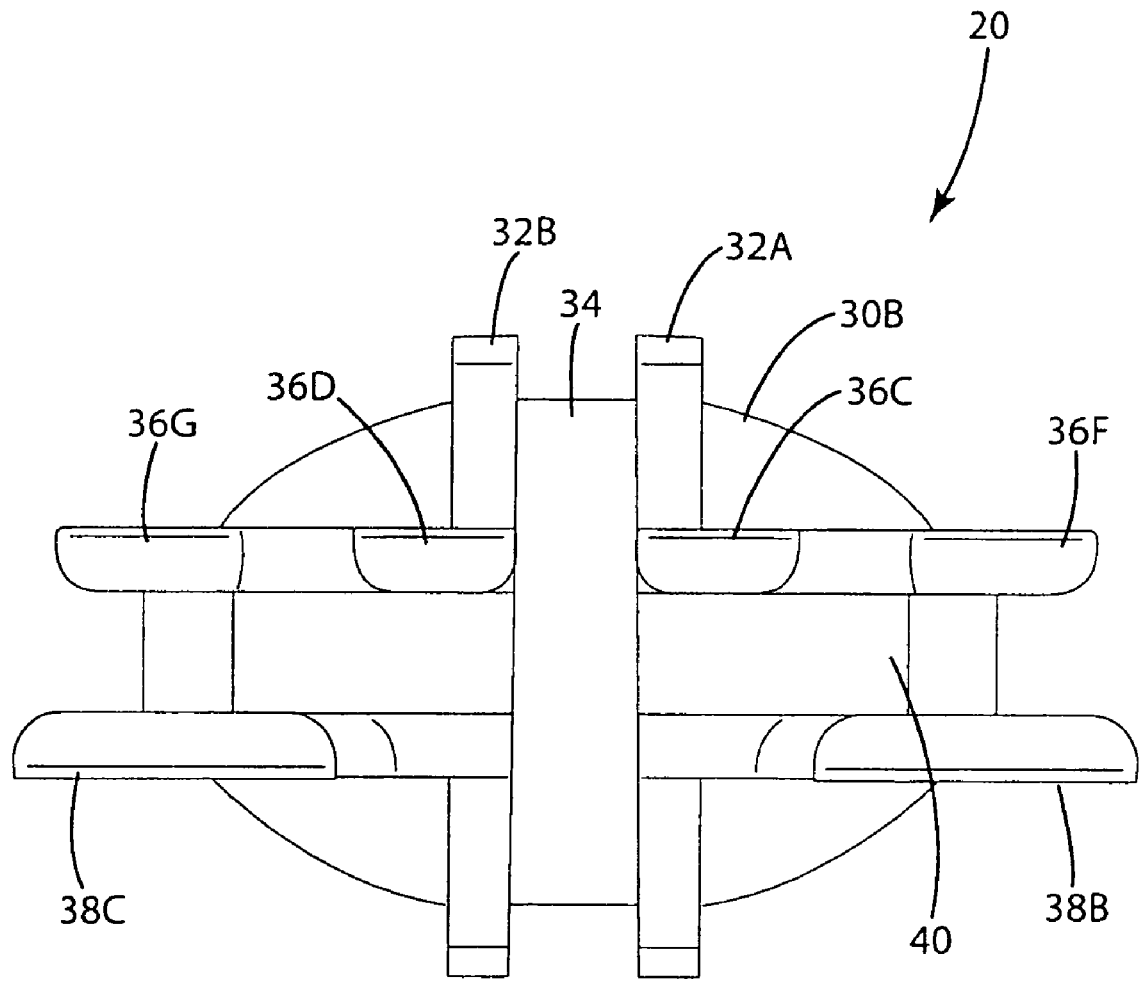
FIG. 4 is a front view of the bobbin.
Figure 5:
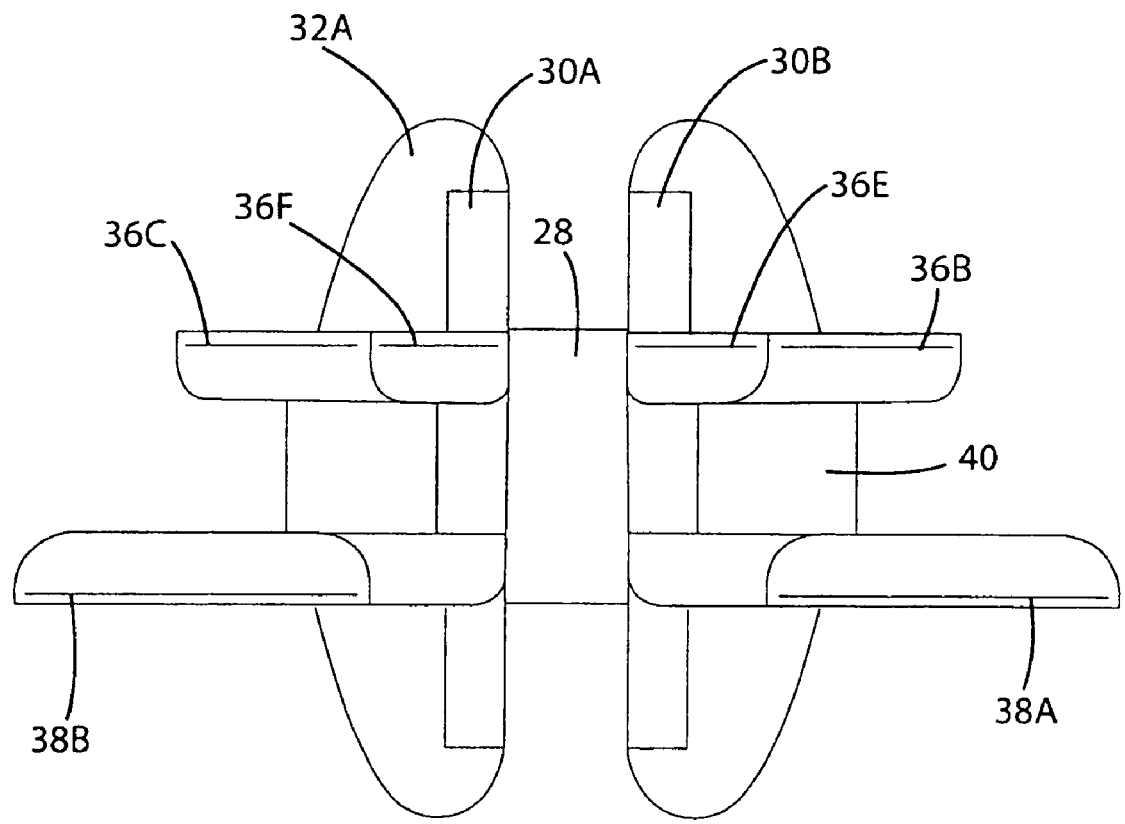
FIG. 5 is a right side elevational view of the bobbin.

To facilitate manufacture, the bobbin 20 may be designed to be molded with a two-piece mold requiring no moving slides, moving pins or other complex moving mold elements. As show in FIGS. 3, 4 and 5, this is achieved by the unique configuration of the bobbin 20, which does not include any undercuts that would prevent removal of the molded part from the mold. FIG. 3 shows a top view of the bobbin 20, which is in a direction parallel to the direction in which the mold opens and closes. FIG. 4 shows a front view the bobbin 20, which is in a direction perpendicular to the direction in which the mold opens and closes. Finally, FIG. 5 shows a side elevations view of the bobbin 20, which like FIG. 4 is in a direction that is perpendicular to the direction in which the mold opens and closes. Referring now to FIG. 2, the bobbin 20 generally defines three separate spools 22, 24 and 26, one for each of the three coils 12, 14 and 16. The first spool 22 includes a core 28 and a pair of opposed guide walls 30a–b that define a somewhat oval channel to receive wire. The core 28 defines an opening 29. The first coil 12 is wrapped around the core 28 with the guide walls 30a–b providing a wrapping guide and helping to retain the coil 12. The second spool 24 is defined by a second core 34 and a second pair of guide walls 32a–b. The second core 34 may be convex to provide a round surface for receiving the second coil 14. Alternatively, the core 34 can be partially defined by the outer surfaces of the guide walls 30a–b of the first spool 22. The second pair of guide walls 32a–b extends perpendicularly to the guide walls 30a–b of the first spool 22. The second coil 14 is wrapped around the second core 34 with the guide walls 32a–b providing a wrapping guide and helping to retain the coil 14. The third spool 26 is defined by a third core 40, inner guide segments 36a–h and outer guide segments 38a–d. The outer surfaces of the core 40 may be convex to provide a curved surface for receiving the coil 16. Alternatively, the core 40 can be partially defined by the outer surfaces of the guide walls 32a–b of the second spool 24. The inner guide segments 36a–h extend along a common plane to cooperatively define a first wiring guide for the third coil 16. Similarly, the outer guide segments 38a–d extend along a common plane to cooperatively define a second wiring guide for the third coil 16. As can be seen, the inner guide segments 36a–h do not overlap the outer guide segments 38a–d along the direction of the axis of the spool 26.

Figure 6:
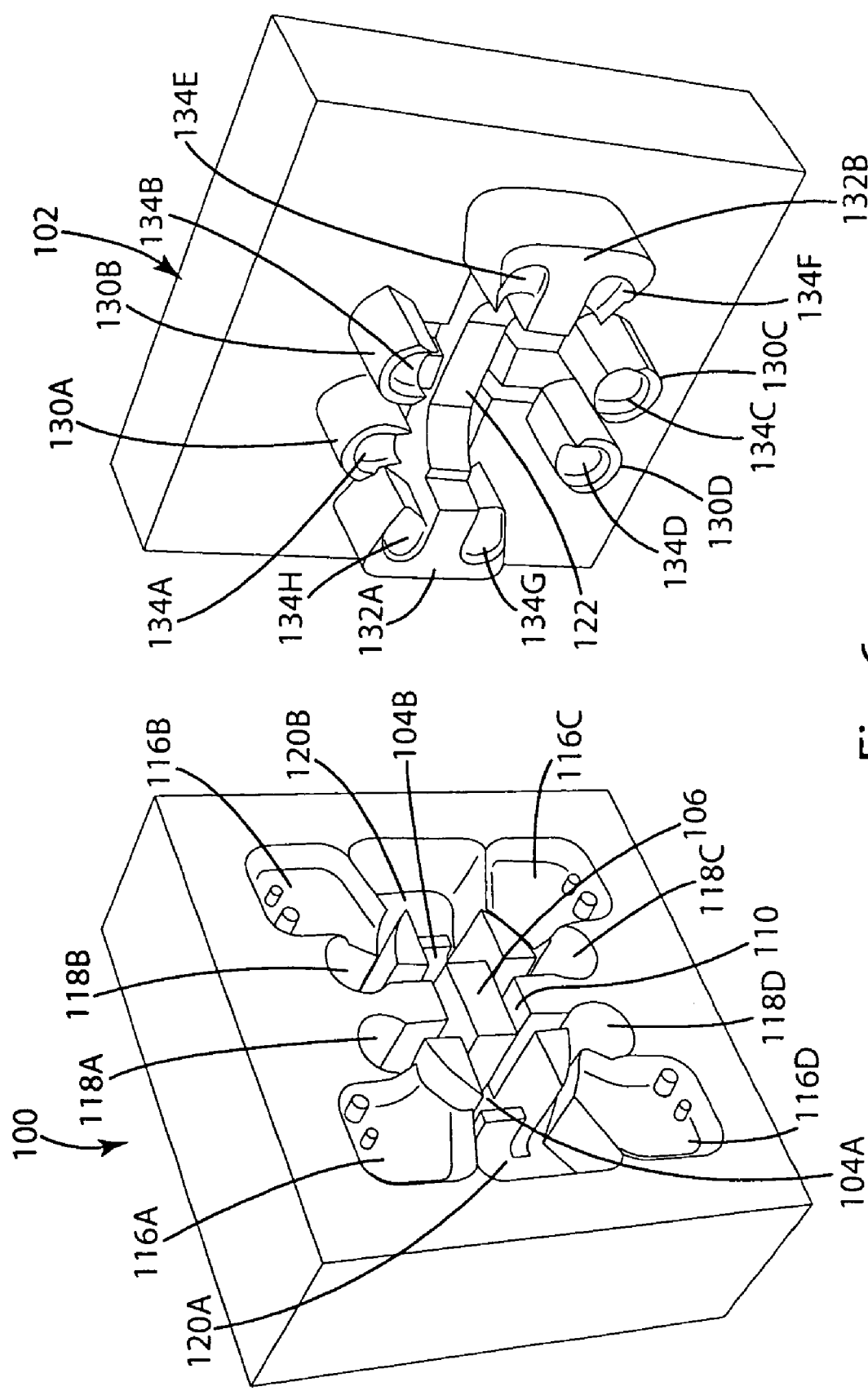
FIG. 6 is a perspective view of two mold pieces for use in molding the bobbin.
Figure 7:
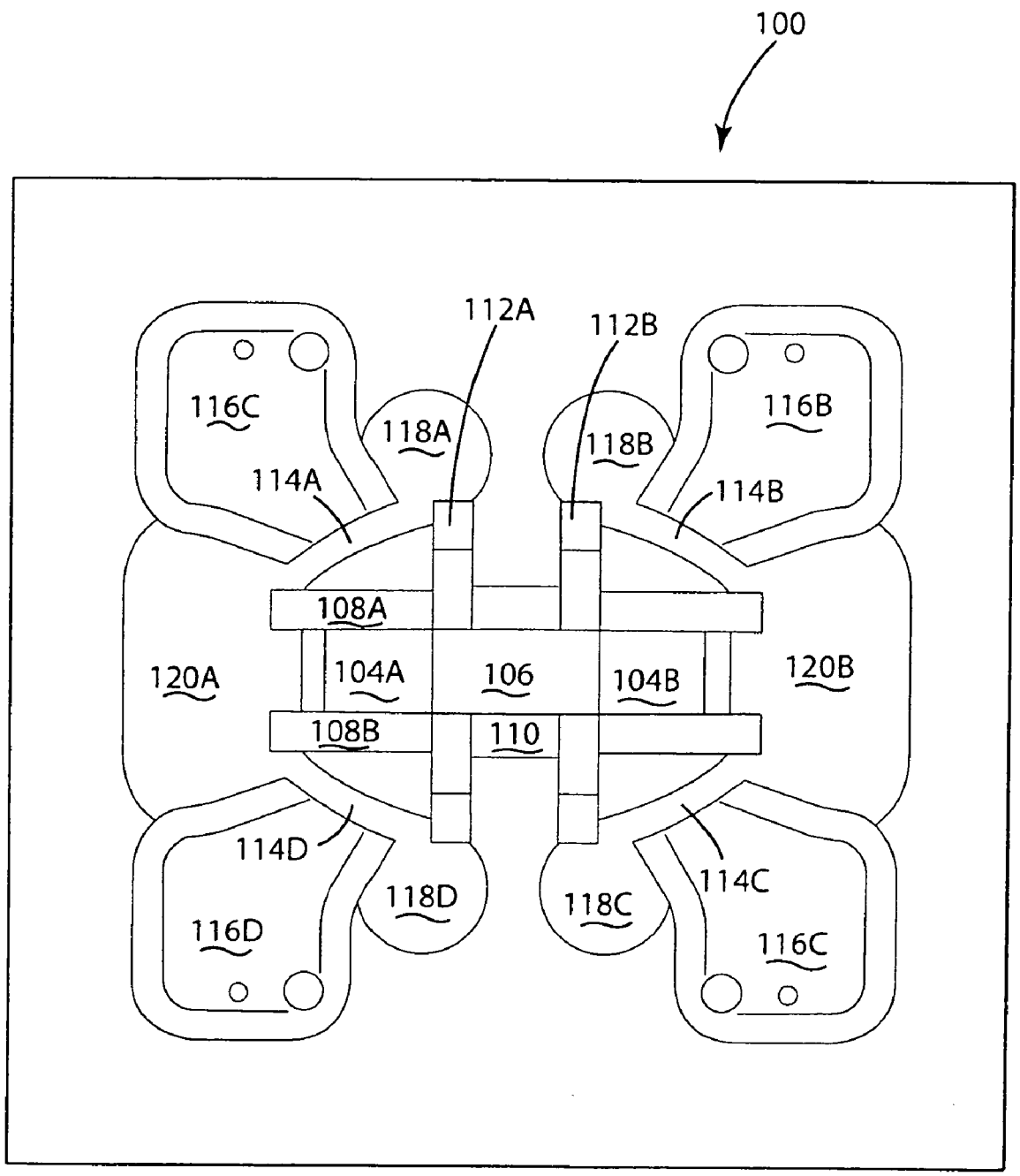
FIG. 7 is a plan view of the first mold piece.
Figure 8:
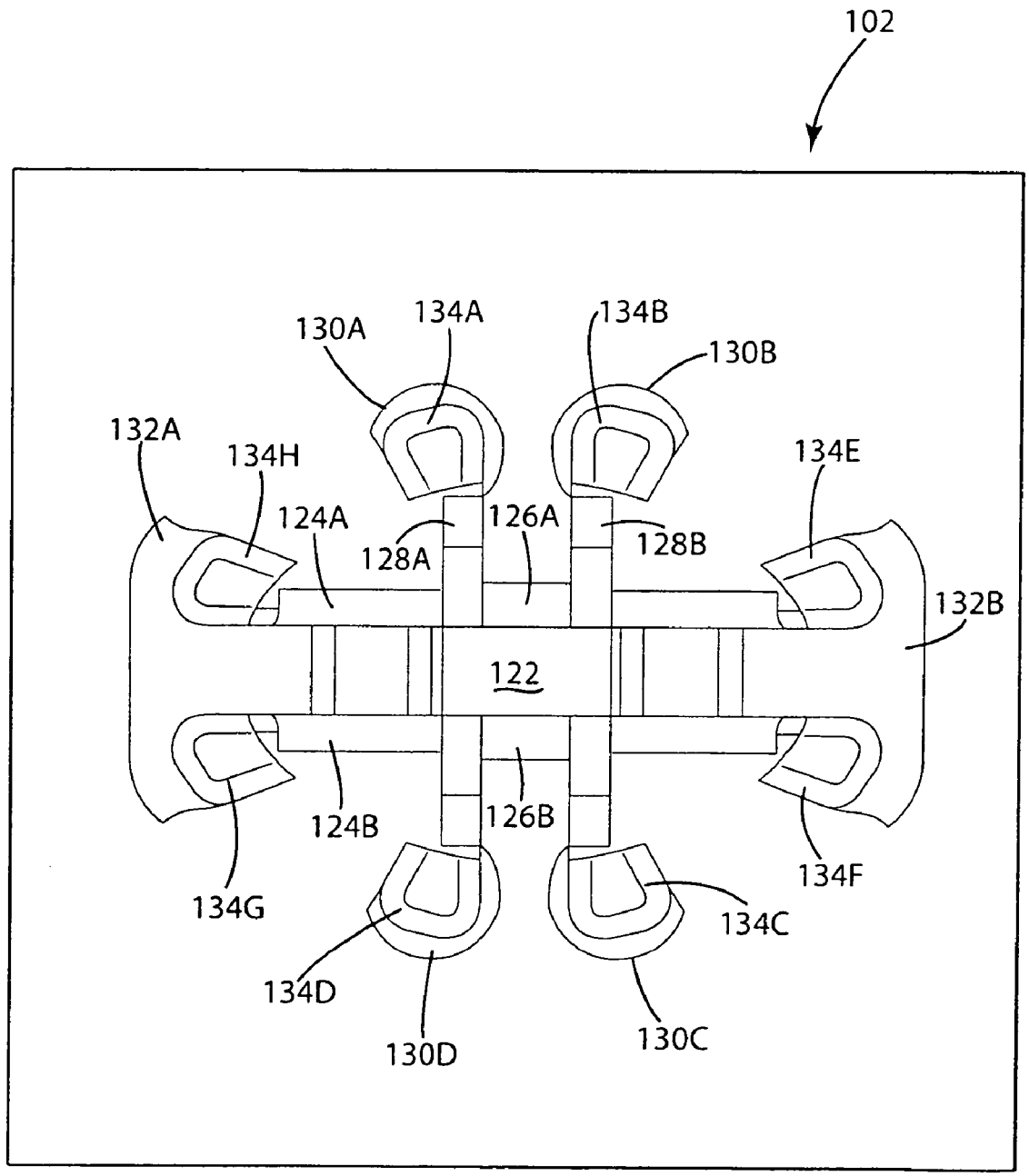
FIG. 8 is a plan view of the second mold piece.

FIG. 6 is a perspective view showing the two mold pieces 100 and 102 in an open position. The mold pieces 100 and 102 close together in a conventional manner to cooperatively define a mold cavity in the shape of the bobbin 20. FIG. 6 illustrates the mold contours, thereby showing how the two mold pieces 100 and 102 cooperate to define a single bobbin 20 three separate spools 22, 24 and 26 without the need for moving slide, moving pins, moving cores or other moving mold components. In general, the first mold piece 100 forms the inner surfaces of the bobbin 20 and the second mold piece 102 forms the outer surfaces. Referring to FIGS. 6–8, the first mold piece 100 includes various contours that contribute to the shape of the first spool 22, including generally arcuate recesses 104a–b to cooperatively form the inner surfaces of the first core 28, block 106 to form an opening in core 28 (primarily to save in weight and material), and generally arcuate channels 108a–b to form the inner surfaces of the guide walls 30a–b. With regard to the second spool 24, the first mold piece 100 defines generally arcuate recess 110 to form the inner surfaces of the second core 34 and generally arcuate channels 112a–b to form the inner surfaces of the guide walls 32a–b. With regard to the third spool 26, the first mold piece 100 defines channel segments 114a–d to form the inner surfaces of the third core 34, recesses 116a–d to form the inner surfaces of outer guide segments 38a–d, and recesses 118a–d to receive protrusions 130a–d of the second mold piece 102 and form the inner surfaces of inner guide segments 36a–d. The first mold piece 100 also defines a pair of recesses 120a–b which receives protrusions 132a–b and forms the inner surfaces of inner guide segments 36e–h.

The second mold piece 102 defines the outer surfaces of the three spools 22, 24 and 26. With regard to spool 22, the second mold piece 102 defines a generally arcuate recess 122 which forms the outer surfaces of core 28 and generally arcuate channels 124a–b which form the outer surfaces of guide walls 30a–b. With regard to spool 24, the second mold piece 102 defines a generally arcuate recess 126 which forms the outer surface of core 34 and generally arcuate channels 128a–b which form the outer surfaces of guide walls 32a–b. With regard to spool 26, the second mold piece includes a set of four protrusion 130a–d that extend into recesses 118a–d in the first mold piece 100 and a pair of protrusions 132a–b that extend into recesses 120a–b. Each protrusion 130a–d defines a recess 134a–d to form the outer surfaces of inner guide segments 36a–d. Similarly, each protrusion 132a–b defines a pair of recesses 134e–h to form the outer surfaces of inner guide segments 36e–h.

Figure 9:
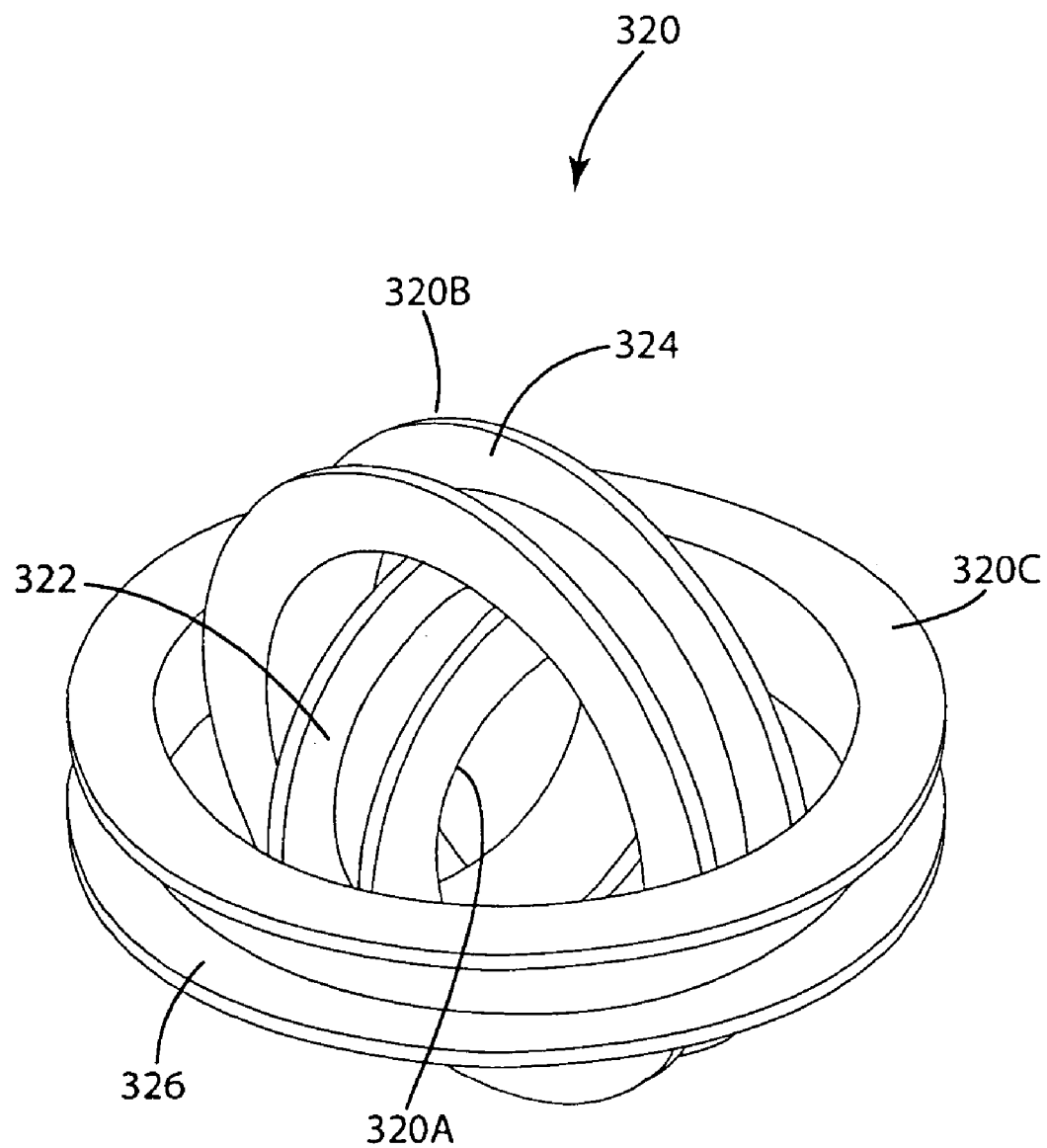
FIG. 9 is a perspective view of an alternative bobbin.
Figure 10:
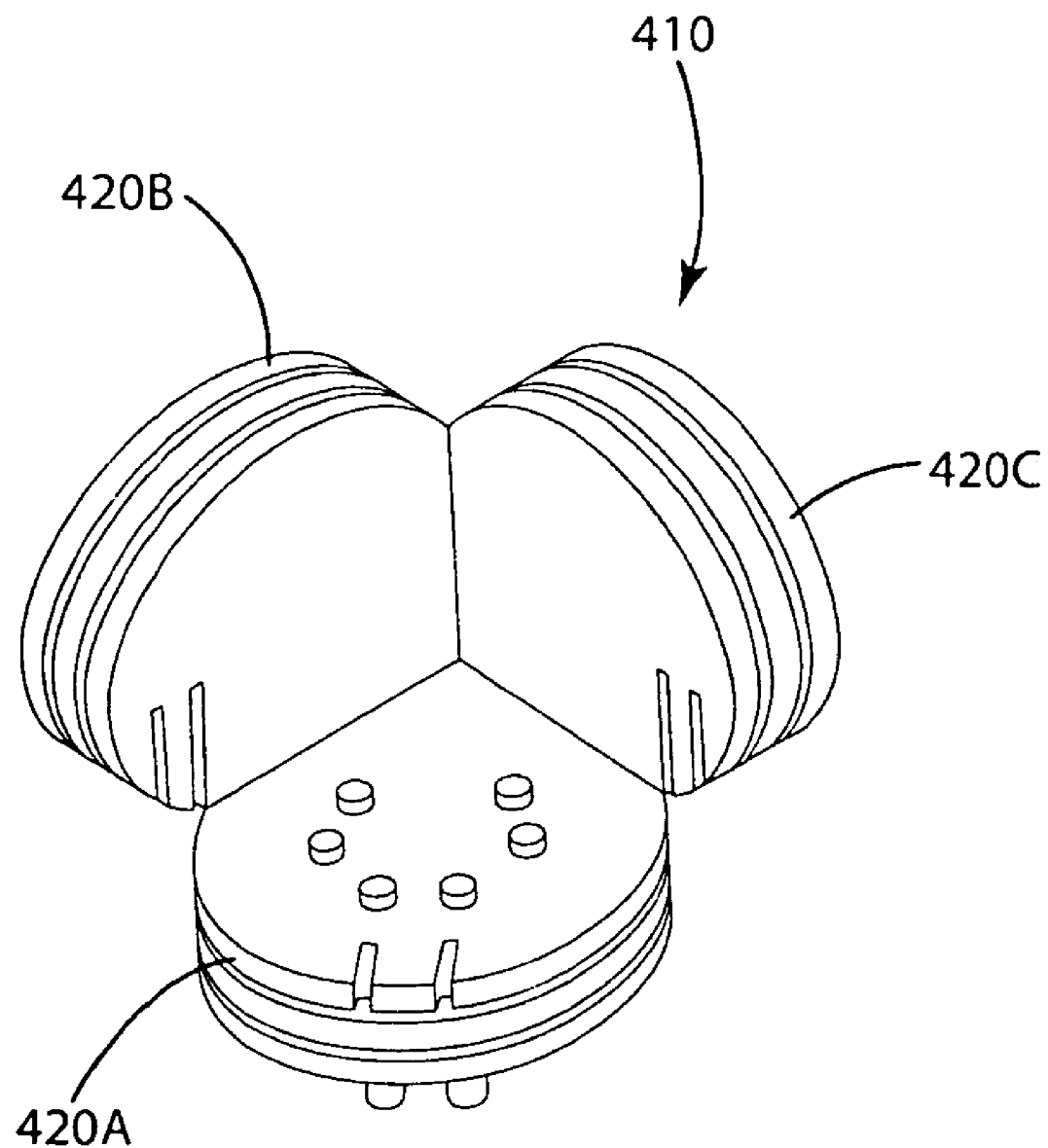
FIG. 10 is a perspective view of a second alternative bobbin.
Figure 11:
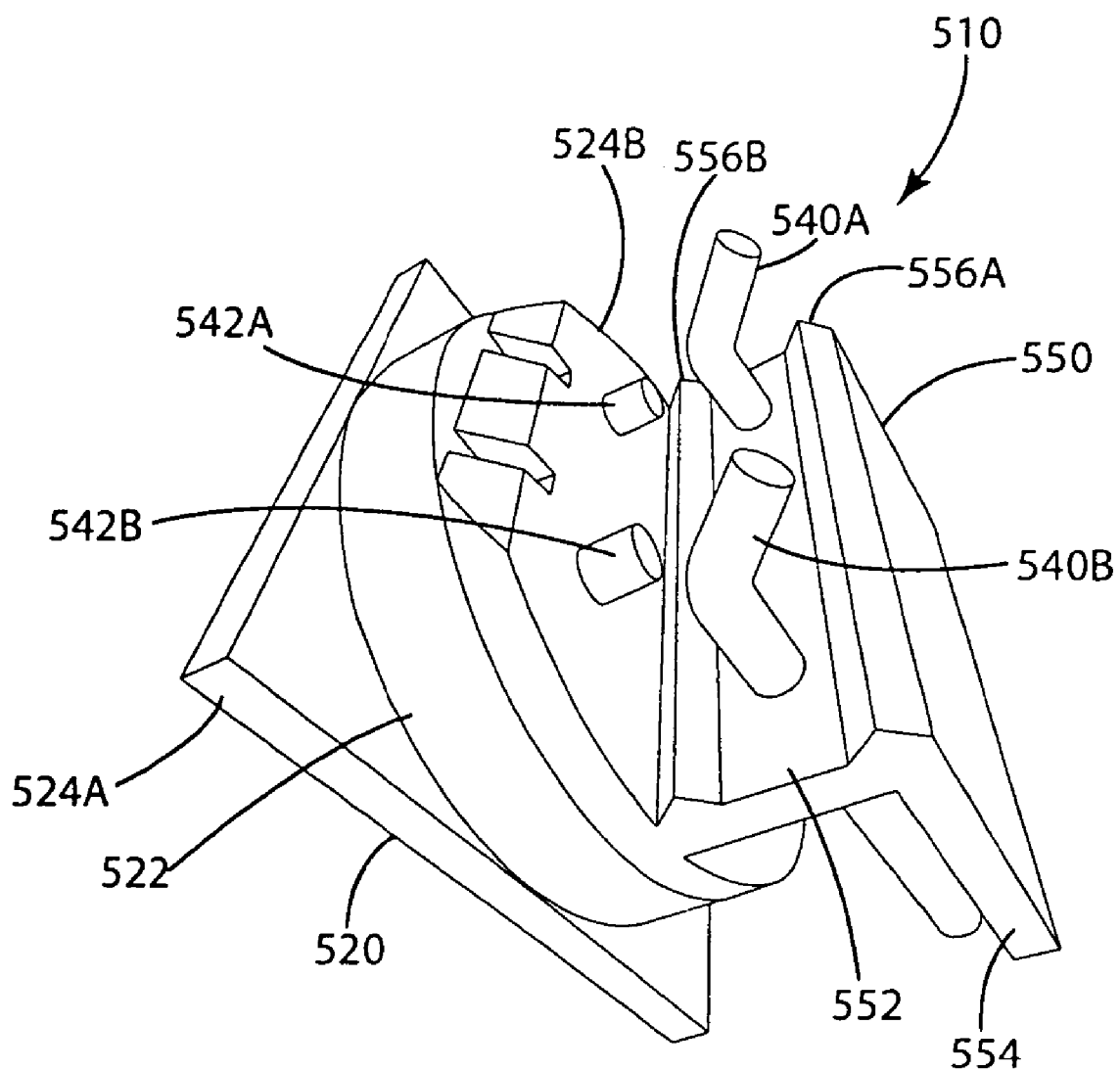
FIG. 11 is a perspective view of a third alternative bobbin.

Although the above described embodiment includes a single bobbin 20 for all three coils. The inductive coil assembly may include alternative constructions. For example, an alternative inductive coil assembly may include a separate, single-spool bobbin for each coil. The three-coil bobbin assembly 320 illustrated in FIG. 9 includes three separate bobbins 320a–c that have different diameters and are fitted one inside the other. Given that the power induced in a secondary coil is proportional to the diameter of the coil, the use of differently sized bobbins may result in an imbalance in the power supplied to each secondary coil. In applications where it is desirable to balance the power induced in the different coils, additional turns of wire can be added to the smaller spools 322, 324 and 326, with the precise number of additional turns added to each smaller bobbin depending primarily on its size. For example, if the coil in the outermost bobbin 320c includes seven turns, it may be desirable to include eight turns on the coil in the middle bobbin 320b and nine turns on the coil in the innermost bobbin 320c. In another alternative embodiment illustrated in FIG. 10, the inductive coil assembly 410 may include three separate bobbins 420a–c that are positioned adjacent to one another, rather than nested inside of one another. Alternatively, the inductive coil assembly may include a spherical bobbin (not shown), with each coil being wrapped about the spherical bobbin at the desired location and in the desired orientation, for example, about the x, y and z axes. This embodiment reduces the differences in the diameters of the three secondaries, thereby improving the balance of the coils. In yet another alternative embodiment, the inductive coil assembly may include three separate, unconnected bobbins that can be place at varied locations. In this embodiment, the bobbins may be a simple annular spool or may include a unique shape that permits them to be easily mounted at different angles. An inductive coil with a unique multi-position bobbin 520 is shown in FIGS. 11 and 12a–d. This bobbin 520 generally includes a single spool 522, a pair of guide walls 524a–b and a mounting arm 550. The configuration of the various components permits the bobbin 520 to be mounted in various orientations, for example, to a circuit board. The mounting arm 550 generally includes two arm segments 552 and 554. In the illustrated embodiment, the first arm segment 552 includes a pair of rails 556a–b. Rail 556a is disposed at the end of the first arm segment 552. The rails 556a–b may be triangular in cross section. For example, rail 556a may extending at 45 degrees with respect to the axis of the spool. To facilitate mounting of the bobbin 520 at an angle, guide wall 524a may terminate in a common plane with the mounting arm 550, and more specifically with the end of the first arm segment 552. The angle of this common plane is set at the desired mounting angle. For example, in the illustrated embodiment, the common plane extends at 45 degrees from the axis of the spool 522. To facilitate mounting, guide wall 524a may be chamfered along the common plane, for example, at 45 degrees. In this way, the angled surface of rail 556a and the chamfered edge of guide wall 524a extend along the common plane to provide a firm structure for supporting the bobbin 520 at a 45 degree angle. The bobbin 520 also includes two sets of electrical pins 540a–b and 542a–b that function as alternative electrical connections or alternative mounting pins or both depending on the orientation of the bobbin 520. FIG. 12a shows bobbin 520 mounted to a circuit board at a 45 degree angle. FIG. 12b shows the bobbin 520 mounted to a circuit board in a vertical position extending partially through the board. FIG. 12c shows the bobbin 520 mounted to a circuit board in a vertical position fully above (or below) the board. And finally, FIG. 12d shows the bobbin 520 mounted to a circuit board in a horizontal position.

In a further embodiment (not shown), the bobbin may include two separately manufactured pieces that are assembled to form the complete bobbin. For example, the bobbin may be formed from two identical mold pieces, with the two mold pieces corresponding to the opposite halves of bobbin 20 when divided by a plane extending parallel to and mid-way between the inner and outer guide segments 36a–h and 38a–d, respectively. Because this alternative bobbin is formed in two separate pieces, the staggered inner and outer guide segments 36a–h and 38a–d, respectively, can be replaced by continuous guide walls. The continuous guide wall can be placed at the mold parting line to facilitate manufacture. In this embodiment, the two bobbin pieces may be separately molded and then welded, glued or otherwise intersecured to form the completed bobbin. As an alternative to conventional adhesives or fasteners, the two bobbin pieces may be held together by the coil windings. For example, the two pieces may be configured so that the first coil is wound in a direction that holds the two bobbin pieces together.

The inductive coil assembly 10 of the present invention can be incorporated into essentially any inductively power device to improve power transfer in various orientations of the device within the magnetic field. For example, a cell phone (not shown), personal digital assistant (not shown), notepad computer (not shown), digital music player (not shown) or electronic gaming device (not shown) can be provided with an inductively powered battery charger having a secondary with multiple coils, such as inductive coil assembly 10. In this context, the cell phone, personal digital assistant, notepad computer, digital music player or electronic gaming device can be placed randomly within the magnetic field created by a primary coil without concern for its orientation because the inductive coil assembly 10 will be able to obtain sufficient power to charge the device in any orientation.

Figure 13A:
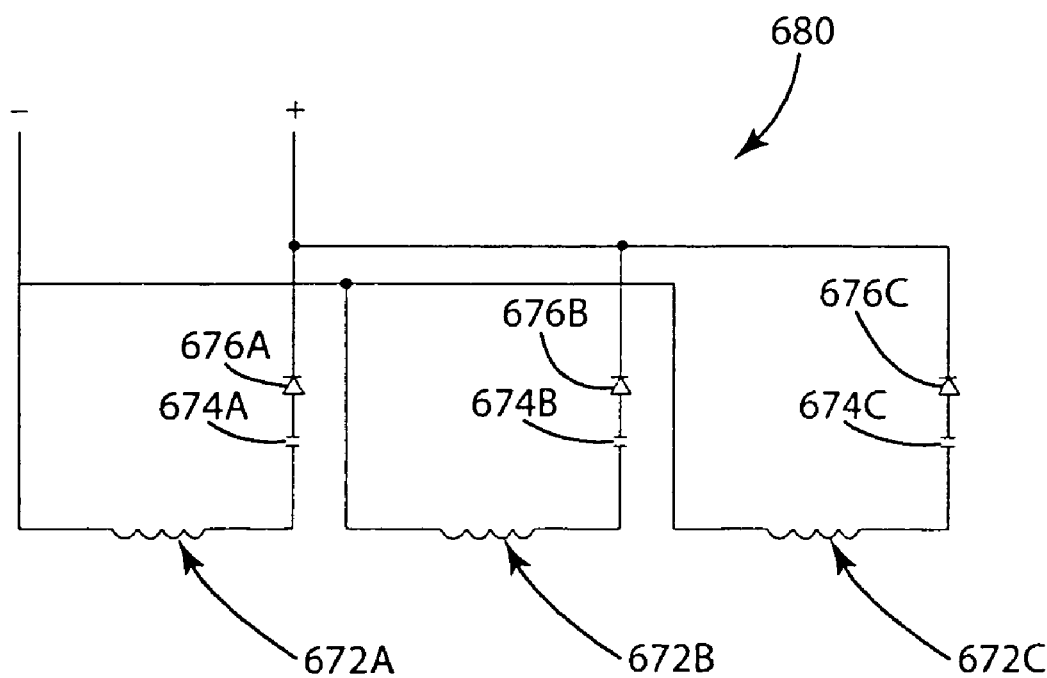
FIGS. 13a–c are circuit diagrams of alternative multi-axis inductive coil assembly circuits for receiving power from an inductive source.
Figure 13B:
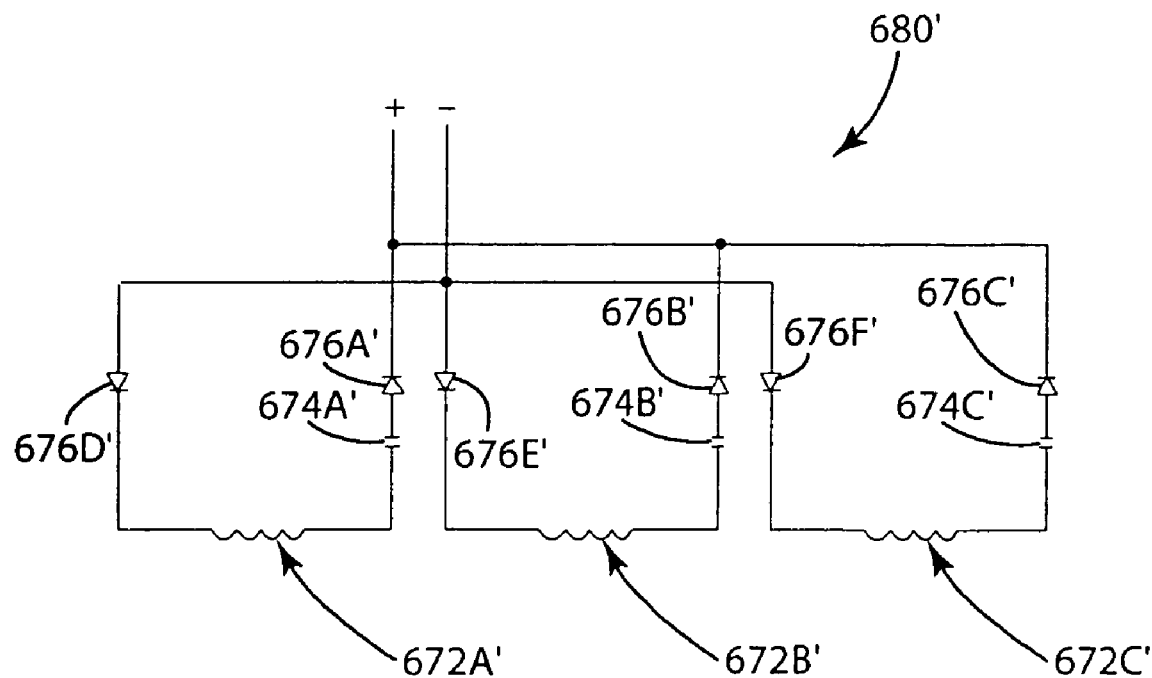
Figure 13C:
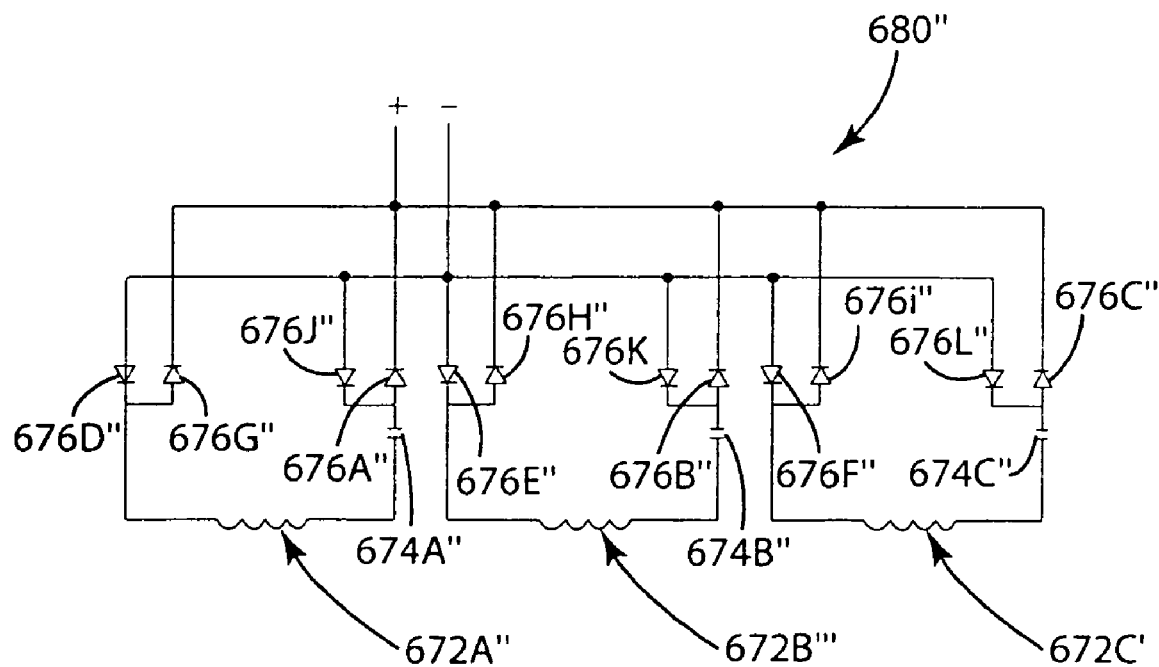

FIGS. 13a–c show circuit diagrams for three embodiments of the inductive coil assembly. FIG. 13a illustrates a circuit 680 that provides DC power from three separate coils 672a–c. As shown, the three coils 672a–c are connected in parallel to the load, a capacitor 674a–c is connected in series between each coil 672a–c and the load. In this embodiment, the value of each capacitor 674a–c and each diode 676a–c is selected to provide a resonant circuit for the load-side of the circuit. Accordingly, their values may be dependent on the characteristics of the load (not shown). This circuit 680 combines the power induced within each of the coils using the capacitors to provide resonance with the load, and diodes 676a–c rectifying the voltage output from circuit 680. Alternatively, diodes 676a–c can be eliminated from the circuit 680 to provide AC power to the load.

FIG. 13b illustrates a half wave rectifier circuit 680' that provides DC power from three separate coils 672a–c'. As shown, the three coils 672a–c' are connected in parallel to the load through an arrangement of diodes 676a–f' connected in series between each coil 672a–c' and the load. In this embodiment, the value of each diode 676a–f' is determined based primarily on the characteristics of the load. Additionally, a capacitor 674a–c' is connected in series between one side of the coil 672a–c' and the corresponding diodes 676a–f'. The value of each capacitor 674a–c' is also determined based primarily on the characteristics of the load. This circuit 680' combines the power induced within each of the coils using the capacitors to provide resonance with the load, and diodes 676a–f' rectifying the voltage output from the circuit 680'.

FIG. 13c illustrates a full wave rectifier circuit 680" that provides DC power from three separate coils 672a–c". As shown, the three coils 672a–c" are connected in parallel to the load through an arrangement of diodes 676a–l" is connected in series between each coil 672a–c" and the load. In this embodiment, the value of each diode 676a–l" is determined based primarily on the characteristics of the load. Additionally, a capacitor 674a–c" is connected in series between one side of the coil 672a–c" and the corresponding diodes 676a–c" and diodes 676j–l". The value of each capacitor 674a–c" is determined based primarily on the characteristics of the load. All three of these circuits 680, 680' and 680" perform the function of providing DC power. Circuit 680 is likely the least expensive design, while circuit 680" provides the best control over the DC output, for example, circuit 680" likely provide less fluctuation in the output compared to the other two embodiments.

Figure 14:
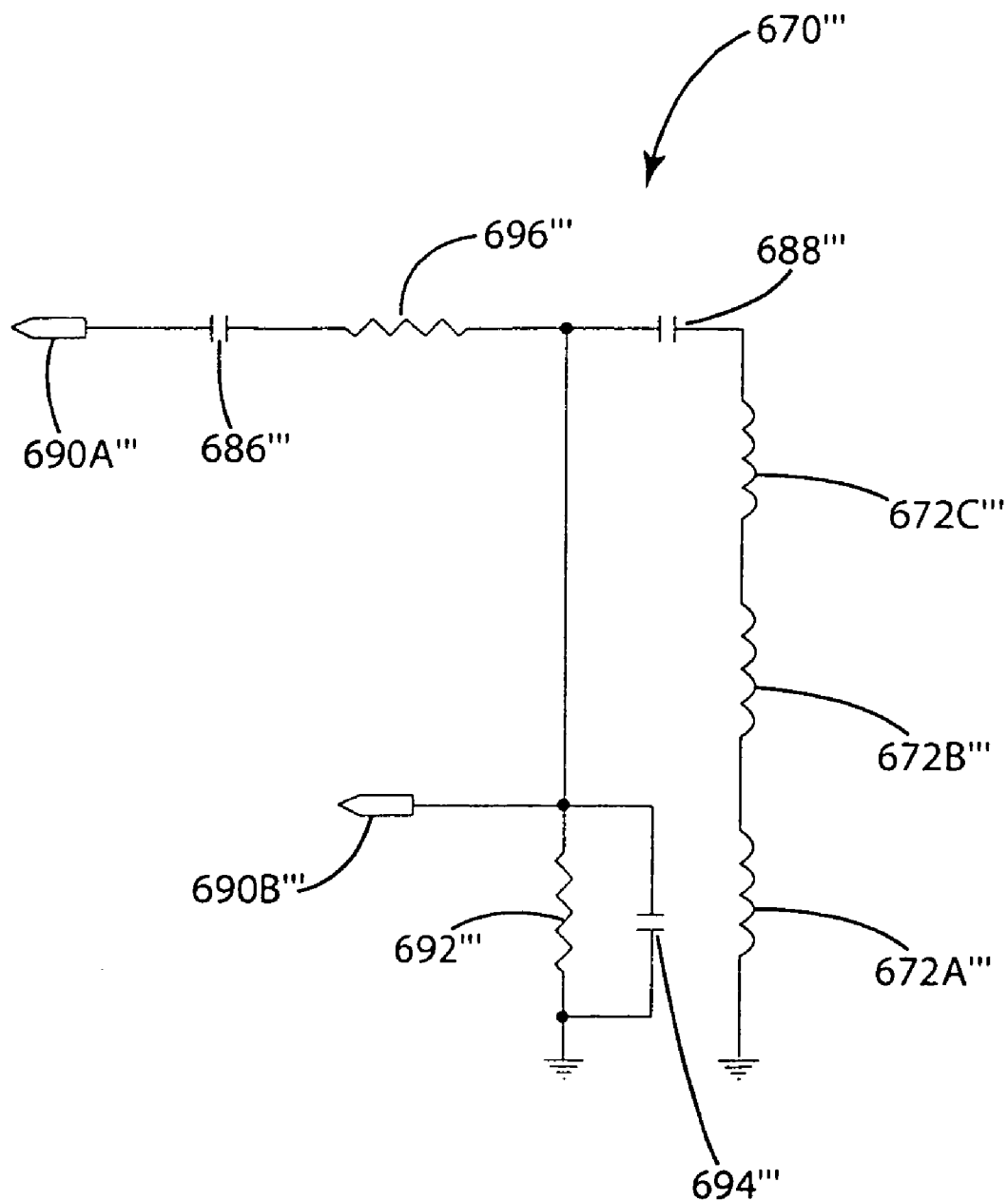
FIG. 14 is a circuit diagram of a multi-axis inductive coil assembly circuit for receiving communication from an inductive source.

In another alternative, the inductive coil assembly can also be used to inductively transfer communications. In one embodiment, this can be achieved using an inductive coil assembly that is essentially identical to the inductive coil assembly 10 described above. In this embodiment, the received communications signals are carried on the power signal. There are a variety of existing communications protocols used with inductive communications to permit the overlay of communications and power. In another embodiment, a second set of coils are used to provide communications. The second set of coils can be formed on the same bobbin used for the power coils, for example, by wrapping a separate communication coil on top of each power coil. The communications coils may require only one or two turns of wire. Alternatively, a second bobbin can be used for the communications coils. The inductive coil assembly of the present invention can readily be used with a wide variety of conventional inductive communications systems. For example, FIG. 14 is a circuit diagram representing a conventional communications circuit for use in applications where the communications signals are separate from the power signals. This circuit enables the simple inductive exchange of communications between a primary and a secondary with a multi-axis inductive coil assembly. The coils 672a–c''' are connected in series to the transceiver 690a–b''', which is represented by RX line 690a''' and TX line 690b'''. The circuit 670''' may include conventional filtering and conditioning components that limit current and increase the signal to noise ratio, thereby improving the performance of the circuit. For example, in the illustrated circuit, the RX line 690b''' may be include resistor 692''' and capacitor 694''' to reduce frequency spikes and noise to increase the signal to noise ratio. Similarly, the circuit 670''' may include resistor 696''' and capacitors 686''' and 688'''' to filter and condition the incoming and outgoing signals. This circuit 670''' combines the communication signals induced within each of the coils 672a–c''' and applies them to RX line 690b''' or applies the signals returned from TX line 690a''' to the coils 672a–c''' to inductively transmit communication signals. The present invention may also be implemented using any of a wide variety of conventional circuits, including circuits in which the coils 672a–c''' are in a parallel relationship. As noted above, the present invention is also well suited for use in applications where the communications signals are carried by the power signals.

Although described primarily in the context of a secondary coil assembly, which inductively receives power or communications or both from an inductive primary, the present invention may also be used as a multi-axis primary coil. In this embodiment (not shown), the different coils generate magnetic fields at different orientations. A single secondary coil is then capable of receiving power or communication or both at different orientations with respect to the primary, for example, as the secondary coil is sufficiently aligned with any one of the magnetic fields generated by the multi-coil inductive primary.

The above description is that of a preferred embodiment of the invention. Various alterations and changes can be made without departing from the spirit and broader aspects of the invention as defined in the appended claims, which are to be interpreted in accordance with the principles of patent law including the doctrine of equivalents. Any reference to claim elements in the singular, for example, using the articles "a," "an," "the" or "said," is not to be construed as limiting the element to the singular.

The invention claimed is:

1. A bobbin for an inductive coil assembly comprising:
a spool having an axis and a pair of guide walls disposed on opposite sides of said spool, said guide walls extending substantially perpendicularly to said axis;
a mounting arm extending from a first one of said guide walls, said mounting arm having a free end terminating in a first common plane with at least one of said guide walls, said first common plane extending parallel to said axis, said mounting arm including a first segment extending substantially perpendicularly to said axis and a second segment extending at an angle from said first segment,
an electrical pin extending through the first segment; and
a first rail extending substantially perpendicular from the first segment.

2. The bobbin of claim 1 wherein said second segment extends substantially perpendicularly to said axis.

3. The bobbin of claim 2 wherein a portion of said first guide wall and a portion of said mounting arm terminate in a second common plane.

4. The bobbin of claim 3 wherein said second common plane extends at approximately 45 degrees with respect to said axis.

5. The bobbin of claim 1 where the first rail has an angled surface.

6. The bobbin of claim 5 where the first rail has a generally triangular cross-section.

7. The bobbin of clam 6 further comprising a second rail, the second rail extending generally perpendicular to the first segment, the second rail having a generally triangular cross-section.

8. A bobbin for an inductive coil assembly comprising:

a spool having an axis and a pair of guide walls disposed on opposite sides of said spool, said guide walls extending substantially perpendicularly to said axis; and a mounting arm extending from a first one of said guide walls, said mounting arm having a free end terminating in a first common plane with at least one of said guide walls, said first common plane extending parallel to said axis, said mounting arm including a first segment extending substantially perpendicularly to said axis and a second segment from said first segment and extending substantially perpendicularly to said axis, wherein a portion of said first guide wall and a portion of said mounting arm terminate in a second common plane, said second common plane extends at approximately 45 degrees with respect to said axis.

* * * * *

UNITED STATES PATENT AND TRADEMARK OFFICE
CERTIFICATE OF CORRECTION

PATENT NO. : 7,116,200 B2　　　　　　　　　　　　　　　　　　　　　Page 1 of 1
APPLICATION NO. : 11/115855
DATED : October 3, 2006
INVENTOR(S) : Baarman et al.

It is certified that error appears in the above-identified patent and that said Letters Patent is hereby corrected as shown below:

Column 8, Claim 1, line 57
 "perpendicularly" should be --parallel--

Column 10, Claim 8, line 6
 "perpendicularly" should be --parallel--

Signed and Sealed this

Twenty-second Day of June, 2010

David J. Kappos
*Director of the United States Patent and Trademark Office*